US00PP28983P2

(12) United States Plant Patent
O'Connell

(10) Patent No.: US PP28,983 P2
(45) Date of Patent: Feb. 20, 2018

(54) ***AEONIUM* PLANT NAMED 'BLACK DIAMOND'**

(50) Latin Name: *Aeonium hybrida*
Varietal Denomination: Black Diamond

(71) Applicant: Renee O'Connell, Escondido, CA (US)

(72) Inventor: Renee O'Connell, Escondido, CA (US)

(73) Assignee: Altman Speciaty Plants, Inc, Vista, CA (US)

( * ) Notice: Subject to any disclaimer, the term of this patent is extended or adjusted under 35 U.S.C. 154(b) by 0 days.

(21) Appl. No.: 15/330,624

(22) Filed: Oct. 18, 2016

(51) Int. Cl.
*A01H 5/02* (2006.01)

(52) U.S. Cl.
USPC ..... Plt./373

(58) Field of Classification Search
USPC ..... Plt./373
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Aeonium* cultivar named 'Black Diamond' is disclosed, characterized by exceptionally dark burgundy foliage and early production of offsets. Plants produce distinctively large rosettes, with a single plant easily filling an eight-inch pot. *Aeonium* is, typically produced as a container plant for the patio or for landscape use.

1 Drawing Sheet

Latin name of the genus and species: *Aeonium hybrida.*
Variety denomination: 'BLACK DIAMOND'.

BACKGROUND OF THE INVENTION

The new cultivar, *Aeonium* 'Black Diamond', was found by the inventor, Renee O'Connell, as the result of a crossing made May 2013 as part of a planned breeding program. The seed parent variety is the unpatented proprietary variety referred to as *Aeonium hybrida* 'Dark 11'. The pollen parent is the unpatented variety *Aeonium hybrida* 'Zwartkin'. *Aeonium* 'Black Diamond' was selected by the inventor, Renee O Connell, in September of 2014 from a group of seedlings resulting from the 2013 crossing, at a commercial greenhouse in Vista. Calif.

Asexual reproduction of the new cultivar 'Black Diamond' was first performed in Vista, Calif., at a commercial greenhouse, by vegetative cuttings in October of 2014. 'Black Diamond' has since produced multiple generations and has shown that the unique features of this cultivar are stable and reproduced true to type.

SUMMARY OF THE INVENTION

The cultivar 'BLACK DIAMOND' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BLACK DIAMOND' These characteristics in combination distinguish 'BLACK DIAMOND' as a new and distinct *Aeonium* cultivar:

1 The rosettes of 'Black Diamond' are comprised of many dark burgundy to nearly black leaves; foliage color darkening with full sun.
2. Offsets at an early size; at approximately 6" tall, creating an attractive dark burgundy black cluster.

3. The diameter of the rosettes can exceed 8" when offsetting begins; therefore a single cut fills an 8" pot readily for commercial finished plant production purposes.
4. 'Black Diamond' forms large rosettes in comparison to many other dark leaved *Aeoniums.*

Plants of the new cultivar 'BLACK DIAMOND' are similar to plants of the seed parent, in most horticultural characteristics, however, plants of the new cultivar 'BLACK DIAMOND' differ in the following;

1. 'Black Diamond' offsets at an early size; at approximately 6" of height, whereas the 'Dark 11' does not offset until it reaches a much greater height.
2. 'Black Diamond' exhibits offsets close to the center of the plant; contributing to an attractive clustering habit, whereas the offsets of 'Dark 11' are held away from the plant center.
3. 'Black Diamond' forms rosettes that are much darker in color than those of 'Dark 11', which are more brown in color.
4. 'Black Diamond' is a much more compact plant than 'Dark 11'.

Plants of the new cultivar 'BLACK DIAMOND' are similar to plants of the pollen parent, in most horticultural characteristics, however, plants of the new cultivar 'BLACK DIAMOND' differ in the following;

1. 'Black Diamond' forms a much larger rosette than 'Zwartkin'.
2. 'Black Diamond', due to the larger rosette, creates a much larger cluster than does *Aeonium* 'Zwartkin', filling space in the landscape more rapidly.
3. 'Black Diamond' forms rosettes that are much darker leaved than those of *Aeonium* 'Zwartkin'.

COMMERCIAL COMPARISON

Plants of the new cultivar 'BLACK DIAMOND' are comparable to the unpatented, commercial variety *Aeonium*

'Zwartkop'. The two *Aeonium* varieties are similar in most horticultural characteristics; however, the new variety 'BLACK DIAMOND' differs in the following:

1. 'Black Diamond' forms larger rosettes as compared than 'Zwartkop'.
2. 'Black Diamond' offsets at a much shorter size than *Aeonium* 'Zwartkop', creating an aesthetically pleasing cluster in an 8" pot, whereas it is necessary to plant multiple cuts of *Aeonium* 'Zwartkop' to achieve the same appearance of "clustering".
3. Due to the earlier offsetting of 'Black Diamond' as compared with *Aeonium* 'Zwartkop', the plant can be propagated more rapidly, shortening production times.
4. 'Black Diamond', when grown in full sun, achieves a darker rosette color than does *Aeonium* 'Zwartkop'.

Plants of the new cultivar 'BLACK DIAMOND' can also be comparable to the unpatented commercial variety *Aeonium* 'Cyclops'. The two *Aeonium* varieties are similar in most horticultural characteristics; however, the new variety 'BLACK DIAMOND' differs in the following:

1. 'Black Diamond' forms much more compact clusters than does *Aeonium* 'Cyclops'.
2. 'Black Diamond' offsets at a younger age and shorter size than does *Aeonium* 'Cyclops'.
3. 'Black Diamond' forms rosettes that are darker in color than those of *Aeonium* 'Cyclops'

BRIEF DESCRIPTION OF THE PHOTOGRAPH

The accompanying photograph illustrates in full color the top view of a typical of plant of *Aeonium* 'Black Diamond' grown in a greenhouse in Vista, Calif. Age of the plant photographed is approximately 2 months from a terminal vegetative offshoot cutting. The photograph was taken using conventional techniques and although colors may appear different from actual colors due to light reflectance it is as accurate as possible by conventional photographic techniques. All photographs provided by the breeder.

DETAILED BOTANICAL DESCRIPTION

In the following description, color references are made to The Royal Horticultural Society Colour Chart, 2007, except where general terms of ordinary dictionary significance are used. The following observations and measurements describe 'Black Diamond' plants in a commercial shadehouse in Vista, Calif. Temperatures ranged from 34° F. to 90° F. night and day. No artificial light, photoperiodic treatments or chemical treatments were given to the plants. Natural light conditions were approximately 2500-4000 foot candles of light. Measurements and numerical values represent averages of typical plant types.

Botanical classification: *Aeonium hybrida* 'BLACK DIAMOND'.

PROPAGATION

Type of propagation typically used: Terminal vegetative divisions.

Time to initiate roots: About 18 days at approximately 24° C.

Root description: Fibrous.

PLANT

Age of plant described: Approximately 4 months.

Container size of the plant described: 20.5 cm.

Growth habit: Upright, caulescent, with a terminal rosette, freely offsetting from below rosette and between leaves of the rosette to produce cluster.

Height: Approximately 16 cm to top of highest leaf. Height in cm to top of inflorescence is unknown as plant has been undergoing propagation, and has not yet flowered.

Plant spread: 31 cm.

Growth rate: Fast.

Branching characteristics: Freely offsetting at early maturity, approximately 6 inches tall.

FOLIAGE

Leaf:

*Arrangement*.—Rosulate.

*Average length*.—Average range 9 to 13 cm.

*Average width*.—Approximately 4.0 cm, near apex.

*Width at base*.—1.4 cm.

*Shape of blade*.—Spatulate.

*Apex*.—Broadly acute, mucronate.

*Base*.—Cuneate.

*Margin*.—Minutely dentate, dentations not sharp.

*Texture of top surface*.—Glabrous.

*Texture of bottom surface*.—Glabrous.

*Appearance of top surface*.—Glossy.

*Appearance of top surface*.—Moderately Glossy.

*Quantity of leaves per plant*.—Approximately 100.

*Color*.—Young foliage upper side: Upper ⅔ of leaf near RHS Green 143C. Base to approximately lower ⅓ of length Yellow-Green 144C. Broad apical margin near Greyed-Purple N186A. Young foliage, under side: Upper ⅔ near RHS Green 143C, base to approximately lower ⅓ of length Yellow-Green 144C. Broad apical margin near Greyed-Purple N186A. Flushing from apex down to approximately ¼ of leaf blade N186C. Mature foliage upper side: Near Greyed-Purple N186A. Base, and approximately lower ¼ of leaf blade near Yellow-Green 144D. Apical margin tinted Black 202A, over N186A. Mature foliage, under side: Near Greyed-Purple N186A. Base near Yellow-Green 1444D. Center section of leaf near N186C.

*Venation*.—There is no visual appearance of venation.

FLOWER

Flowering not observed to date.

REPRODUCTIVE ORGANS

Flowering not observed to date.

OTHER CHARACTERISTICS

Fruits and seeds: Plant has not flowered to date.

Temperature tolerance: Tolerates temperatures from approximately −2 degrees C. to 32 degrees C.

Disease/pest resistance: Displays the same disease and pest resistance of any other comparable *Aeonium*.

Drought tolerance: Tolerates at least 3 weeks of high temperatures without supplemental water, showing no serious damage to plant.

What is claimed is:

1. A new and distinct cultivar of *Aeonium* plant named 'BLACK DIAMOND' as herein illustrated and described.

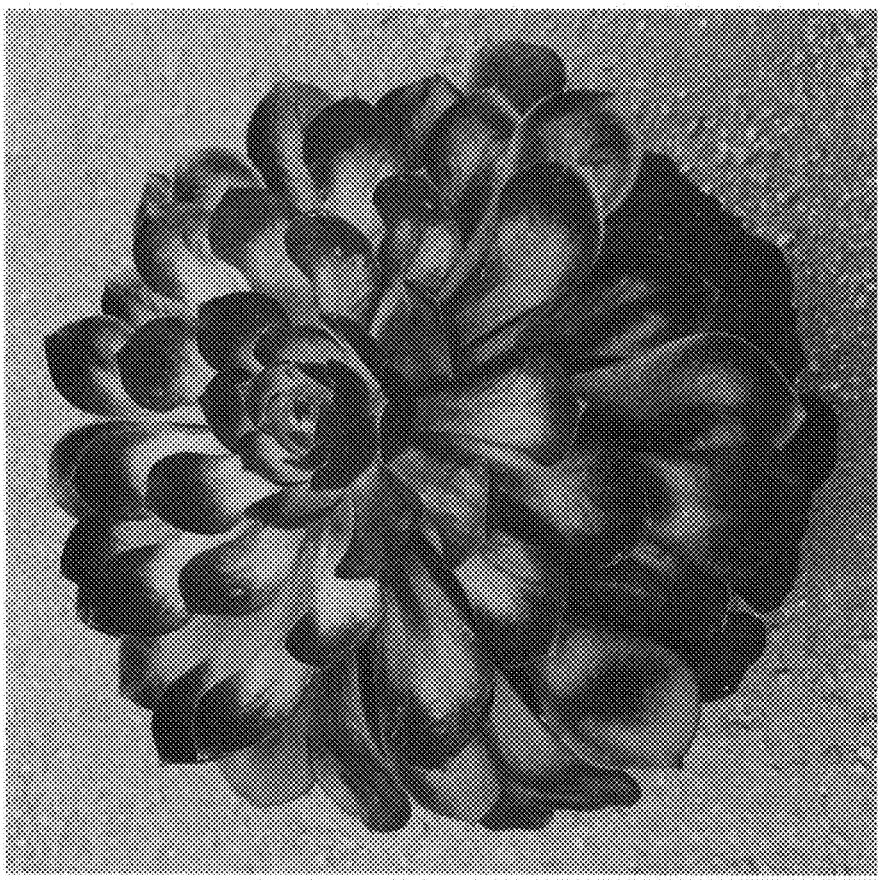

* * * * *